(12) United States Patent
Bower et al.

(10) Patent No.: US 11,291,413 B2
(45) Date of Patent: Apr. 5, 2022

(54) SYSTEMS AND METHODS FOR LINEAR-TIME CLUSTERING FOR BOUNDED, REPEATABLE, RARE EVENTS IN PHYSIOLOGICAL SIGNALS

(71) Applicant: Mayo Foundation for Medical Education and Research, Rochester, MN (US)

(72) Inventors: Mark R. Bower, Rochester, MN (US); Regina S. Bower, Timnath, CO (US); Michael T. Kucewicz, Rochester, MN (US); Gregory A. Worrell, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 692 days.

(21) Appl. No.: 16/062,220

(22) PCT Filed: Dec. 15, 2016

(86) PCT No.: PCT/US2016/066914
§ 371 (c)(1),
(2) Date: Jun. 14, 2018

(87) PCT Pub. No.: WO2017/106490
PCT Pub. Date: Jun. 22, 2017

(65) Prior Publication Data
US 2018/0368778 A1    Dec. 27, 2018

Related U.S. Application Data

(60) Provisional application No. 62/267,597, filed on Dec. 15, 2015.

(51) Int. Cl.
*A61B 5/00* (2006.01)
*A61B 5/04* (2006.01)
*A61B 5/24* (2021.01)

(52) U.S. Cl.
CPC .............. *A61B 5/7225* (2013.01); *A61B 5/24* (2021.01); *A61B 5/7203* (2013.01); *A61B 5/7264* (2013.01); *A61B 5/4806* (2013.01)

(58) Field of Classification Search
CPC ... A61B 5/7225; A61B 5/7264; A61B 5/7203; A61B 5/04001; G16H 50/20
See application file for complete search history.

(56) References Cited

U.S. PATENT DOCUMENTS 5,311,876 A    5/1994  Olsen et al.
6,735,467 B2   5/2004  Wilson
(Continued)

OTHER PUBLICATIONS

Aflalo, et al., Decoding Motor Imagery from the Posterior Parietal Cortex of a Tetraplegic Human, Science, 2015, 348(6237):906-910.
(Continued)

*Primary Examiner* — Regis J Betsch
*Assistant Examiner* — Jeremy A Delozier
(74) *Attorney, Agent, or Firm* — Quarles & Brady LLP

(57) ABSTRACT

Described herein are methods and systems for clustering events in temporal signals, such as physiological signals. In some embodiments, a method for identifying events of interest from noisy physiological signal data is provided, the method comprising: receiving physiological signal data; generating filtered signal using a filter defined by a spectral band; generating signal peak data by identifying, for each of a plurality of time windows, a signal peak in the filtered data; grouping waveforms corresponding to the time windows based on the signal peak data to generate clustered event data; determining parameters for a noise beta distribution; identifying a cluster of waveforms that does not fall within
(Continued)

the noise beta distribution; generating a graphical representation based on the waveforms in the cluster; and displaying the graphical representation.

20 Claims, 6 Drawing Sheets

(56) References Cited

U.S. PATENT DOCUMENTS

| | | | |
|---|---|---|---|
| 2005/0008573 A1 | 4/2005 | Baker, Jr. et al. | |
| 2008/0177196 A1* | 7/2008 | Burdick | A61B 5/4893 600/544 |
| 2008/0228100 A1 | 9/2008 | Navakatikyan | |
| 2014/0007395 A1 | 3/2014 | Rodriguez-Llorente et al. | |
| 2014/0073958 A1* | 3/2014 | Rodriguez-Llorente | A61B 5/7221 600/479 |
| 2014/0163407 A1* | 6/2014 | Figgatt | A61B 7/026 600/528 |
| 2015/0008802 A1 | 1/2015 | Fukuda | |
| 2015/0014863 A1 | 3/2015 | Benaron | |
| 2016/0045120 A1* | 2/2016 | Friedman | A61B 5/4064 600/544 |

OTHER PUBLICATIONS

Bower, et al., Evidence for Consolidation of Neuronal Assemblies After Seizures in Humans, Journal of Neuroscience, 2015, 35(3):999-1010.

Brinkmann, et al., Large-Scale Electrophysiology: Acquisition, Compression, Encryption, and Storage of Big Data, J. Neurosci. Methods, 2009, 180(1):185-192.

Cash, et al., The Emergence of Single Neurons in Clinical Neurology, Neuron, 2015, 86(1):79-91.

Efron, Large-Scale Inference: Empirical Bayes Methods for Estimation, Testing, and Prediction, vol. 1. Cambridge University Press, 2012, 273 pages.

Harris, et al., Accuracy of Tetrode Spike Separation as Determined by Simultaneous Intracellular and Extracellular Measurements, Journal of Neurophysiology, 2000, 84:401-414.

Hill, et al., Quality Metrics to Accompany Spike Sorting of Extracellular Signals, J. Neurosci., 2011, 31(24):8699-8705.

Merricks, et al., Single Unit Action Potentials in Humans and the Effect of Seizure Activity, Brain, 2015, 138:2891-2906.

European Patent Office, Extended European Search Report, Application No. 16876675.6, dated Jul. 9, 2019, 5 pages.

International Search Report/Written Opinion from parent PCT/US2016/066914, dated Feb. 28, 2017, 10 pages.

\* cited by examiner

SYSTEMS AND METHODS FOR LINEAR-TIME CLUSTERING FOR BOUNDED, REPEATABLE, RARE EVENTS IN PHYSIOLOGICAL SIGNALS

CROSS-REFERENCE TO RELATED APPLICATIONS

The present application is a 371 U.S. National Phase Entry of PCT/US16/66914, filed Dec. 15, 2016, which claims priority to U.S. Provisional Application No. 62/267,597, filed Dec. 15, 2015, each of which is hereby incorporated herein by reference in its entirety for all purposes.

BACKGROUND

Current techniques for clustering extracellular action potential ("AP") measurements were developed for animal recordings during learned behaviors. These techniques assume that recordings come from tetrodes, where the challenge is to separate multiple waveforms based on AP shape features (e.g., peak voltage). The current techniques also typically threshold data in real-time and store only one millisecond of data around likely action potentials to reduce disk storage space, discarding residual data as "noise." These clustering algorithms also assume total recording durations of less than 12 hours, allowing all candidate AP detections to be held in computer memory at one time to allow optimization algorithms to be used.

These assumptions, however, are not applicable to clinical recordings that are made over the span of multiple days to attempt to capture physiological data generated during seizures. Such clinical recordings normally come from single microwires, not tetrodes, and these microwires normally isolate at most one neuron, which increases the need to separate action potentials from noise. Data acquisition systems can now record continuously with broadband filters and store the data to a compressed format, which is incompatible with many existing AP clustering algorithms. Multi-day recordings also generate millions of AP detections, which increases the clustering times required for existing optimization algorithms (e.g., "Klusta-Kwik") to unusable lengths.

Thus, there remains a need for clustering techniques that are capable of efficiently clustering bounded, repeated, rare events, such as action potentials and other features in electrophysiological signals.

SUMMARY

In accordance with some embodiments of the disclosed subject matter, methods and systems for linear-time clustering for bounded, repeatable, rare events in physiological signals are provided.

In accordance with some embodiments of the disclosed subject matter, a method for identifying events of interest from noisy physiological signal data is provided, the method comprising: (a) receiving, by a computing system, physiological signal data; (b) generating filtered signal data by filtering the physiological signal data using a filter defined by a spectral band associated with a particular physiological event; (c) generating signal peak data with the computer system by identifying, for each of a plurality of time windows in the filtered data, a signal peak in the filtered data; (d) grouping waveforms from the physiological signal data corresponding to each of the plurality of time windows based on the signal peak data to generate clustered event data; (e) determining parameters for a noise beta distribution based at least in part on the signal peak data; (f) identifying at least one cluster of waveforms from the clustered event data that does not fall within the noise beta distribution, wherein each waveform in the at least one cluster represents a physiological events of interest in the physiological signal data; (g) generating a graphical representation based on the waveforms in the at least one cluster of waveforms; and (h) causing the graphical representation to be displayed.

In some embodiments, the physiologic signal data represents an extracellular recording of electrical activity of a signal neuron.

In some embodiments, the physiologic signal data is received from a single microwire.

In some embodiments, the graphical representation shows a plurality of the waveforms in the at least one cluster of waveforms.

In some embodiments, the graphical representation shows an average waveform that represents a plurality of the waveforms in the at least one cluster of waveforms.

In some embodiments, the physiologic signal data represents at least twenty four hours of signals.

In some embodiments, the spectral band is from about 600 Hertz to about 6,000 Hertz.

In some embodiments, the time window is about one millisecond.

In some embodiments, the method further comprises repeating (a) through (h) for second physiologic signal data that represents an extracellular recording of electrical activity of a second signal neuron.

In some embodiments, generating signal peak data further comprises generating an $N \times 1$ vector, where N is the number of time windows in the plurality of time windows.

In some embodiments, each value in the $N \times 1$ vector represents the peak value of the physiologic signal in a particular time window.

In some embodiments, grouping the waveforms from the physiological signal data further comprises grouping waveforms corresponding to time windows having similar values in the $N \times 1$ vector.

In some embodiments, the method further comprises: using probabilities associated with the at least one cluster as an input to a Bayesian Estimator; and identifying, based on the output of the Bayesian estimator, a second cluster of waveforms from the clustered event data that does fall within the noise beta distribution as likely representing physiological events of interest in the physiological signal data.

In accordance with some embodiments of the disclosed subject matter, a system for identifying events of interest from noisy physiological signal data is provided, the system comprising: a display; and a hardware processor that is programmed to: (a) receive physiological signal data; (b) generate filtered signal data by filtering the physiological signal data using a filter defined by a spectral band associated with a particular physiological event; (c) generate signal peak data with the computer system by identifying, for each of a plurality of time windows in the filtered data, a signal peak in the filtered data; (d) group waveforms from the physiological signal data corresponding to each of the plurality of time windows based on the signal peak data to generate clustered event data; (e) determine parameters for a noise beta distribution based at least in part on the signal peak data; (f) identify at least one cluster of waveforms from the clustered event data that does not fall within the noise beta distribution, wherein each waveform in the at least one cluster represents a physiological events of interest in the physiological signal data; (g) generate a graphical representation based on the waveforms in the at least one cluster of waveforms; and (h) cause the graphical representation to be displayed using the display.

The foregoing and other aspects and advantages of the invention will appear from the following description. In the description, reference is made to the accompanying drawings that form a part hereof, and in which there is shown by way of illustration particular embodiments. Such embodiments do not necessarily represent the full scope of the invention, and reference is made therefore to the claims and herein for interpreting the scope of the invention.

DETAILED DESCRIPTION

Described herein are methods and systems for clustering events in temporal signals, such as electrophysiological signals. In general, the techniques described herein characterize the probability distribution of all waveforms and identify clusters in the outliers. Accordingly, the processes described herein can be referred to as the "Noise Outlier Algorithm," or "NOA." The techniques described herein improve on existing clustering algorithms in at least three ways. First, the techniques described herein can run in linear time, rather than exponential time, providing savings in the amount of computational time required to analyze large data sets (e.g., as described below in connection with FIG. 8). Second, the techniques described herein do not require users to set a priori parameters (e.g., voltage thresholds, expected number of clusters) that are required by other clustering techniques. Third, the techniques described herein can be run adaptively, for example, by updating the noise distribution and/or the probability that data belongs in an identified cluster based on new data.

The techniques described herein can identify signals that are compact or bounded, in the mathematical sense; repeatable; and relatively improbable. Examples include a number of biological phenomena, including, but not limited to extracellular recordings of neuronal action potentials and electroencephalography ("EEG") events, such as sharp waves and inter-ictal spikes. Potential applications of the techniques described herein include analyzing biological, physical, and chemical processes. In some embodiments, the techniques described herein can be adapted for internet or software utilization measures, such as identifying "bursts" of activity that have some regularity as a function of time.

Figure 1:
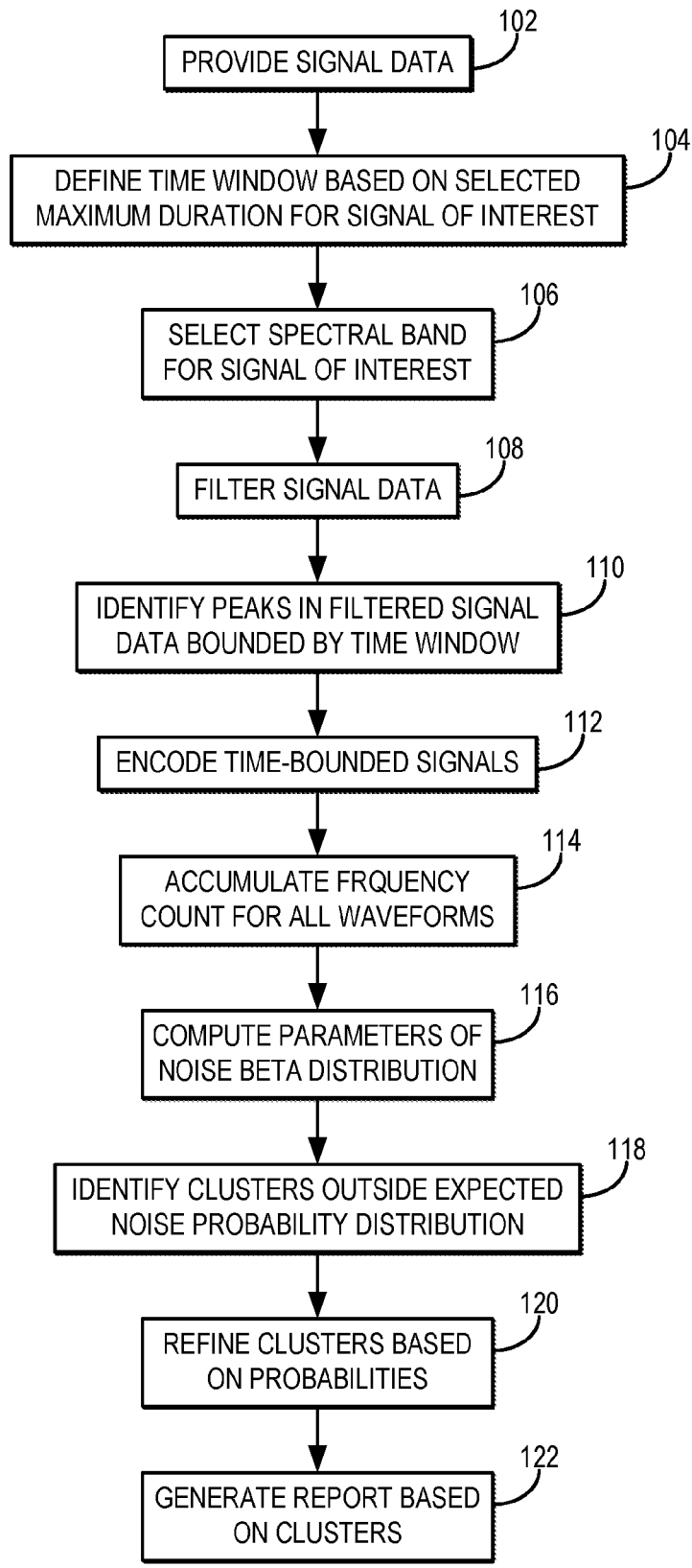
FIG. 1 is a flowchart setting forth the steps of an example process for clustering events in a temporal signal, such as a physiological signal.

Referring now to FIG. 1, a flowchart is illustrated as setting forth the steps of an example process for clustering events in a temporal signal, such as a physiological signal. Examples of electrophysiological signals include those recorded with an EEG system, an electrocardiography ("ECG") system, an electromyography ("EMG") system, and so on. The process thus can begin with providing signal data to a computer system for processing, as indicated at step 102, which can receive the signal data from any suitable source. For example, in some embodiments, providing the signal data can include retrieving previously acquired electrophysiological signals from data storage (e.g., memory), or acquiring such signals in real-time (e.g., from one or more sensors).

A time window is defined by selecting a maximum duration for the signal of interest, as indicated at step 104. As one example, the duration may be 1 millisecond when the goal is to cluster action potential in EEG signals. Other possible durations will be appreciated by those skilled in the art depending on the clinical application, the input electrophysiological signal, and the event to be clustered from the electrophysiological signal. In some embodiments, the time window can be defined based on a user input. For example, a computing device (e.g., the computing device described below in connection with FIG. 9) executing at least a portion of the process described in FIG. 1 can prompt a user to select a time window and/or what type of signal data is being analyzed (which may be associated with a time window) prior to performing any analysis on the signal data. As another example, a user can input a default value of a time window to be used, which can be a default value based on the type of signal data to be analyzed and/or a universal default value to be used.

A spectral band is also defined by selecting a range of frequencies to be filtered, as indicated at step 106. As one example, the spectral band may be 600-6000 Hz when the goal is to cluster action potential in EEG signals. Other possible spectral bands will be appreciated by those skilled in the art depending on the clinical application, the input electrophysiological signal, and the event to be clustered from the electrophysiological signal. In some embodiments, the spectral band can be defined based on user input. For example, a computing device (e.g., the computing device described below in connection with FIG. 9) executing at least a portion of the process described in FIG. 1 can prompt a user to select a spectral band and/or what type of signal data is being analyzed (which may be associated with a spectral band) prior to performing any analysis on the signal data. As another example, a user can input a default value of a spectral band to be used, which can be a default value based on the type of signal data to be analyzed and/or a universal default value to be used.

Based on the spectral band, the provided signal data is filtered, as indicated at step 108. For instance, a bandpass filter is designed based on the selected spectral band and those frequencies outside of the spectral band are removed by applying the bandpass filter to the signal data. Then, using the time window defined by the selected maximum duration, peaks in the signal data that fall within the time window are identified, as indicated at step 110. Thus, the time window is used as a sliding window to process the signal data and identify those signal peaks that can be contained within the time window.

Figure 2:
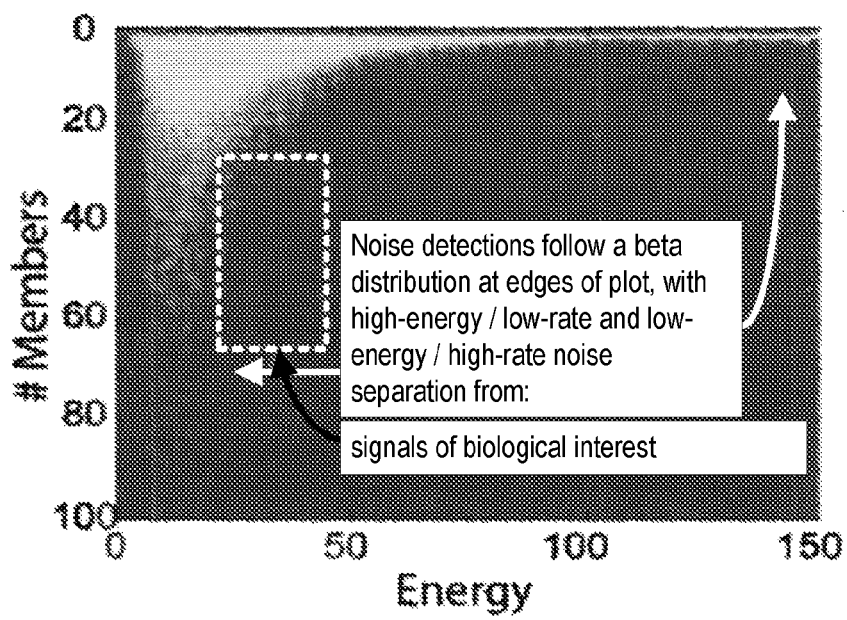
FIG. 2 is an example two-dimensional histogram generated from physiological signal data.

The time-bounded signals associated with the identified peaks are then encoded, as indicated at step 112. As an example, the time-bounded signals can be encoded by binning values at each time point in the signal (e.g., at each window), thereby creating an N×1 vector, where N is the number of time points. In such an example, the value at each position N can represent the peak value within a particular time window. The frequencies of all waveforms are then accumulated to generate counts, as indicated at step 114. In some embodiments, the N×1 vector can be used as a key when accumulating the frequencies of all waveforms at 114. For example, waveforms in time windows having similar peak values can be grouped together based on the values corresponding to those time windows in the N×1 vector. As another example, other parameters and/or additional parameters can be used when grouping the waveforms, such as the period of a signal in the waveform, the amplitude of a signal in the waveform, the signal energy of a signal in the waveform, the signal power of a signal in the waveform, the average value of the waveform, etc. An example two-dimensional histogram computed by encoding a plurality of time-bounded signals and accumulating the frequencies of waveforms in the encoded signals is illustrated in FIG. 2. The histogram shows the distribution of noise around the edges and outliers near the middle. These regions are analyzed to provide clustering of the input physiological signal data, as described now in detail.

The parameters for a beta distribution representative of the noise in the provided signal data are next computed, as indicated at step 116. Using the counts of each cluster, those clusters that lie outside of the noise probability distribution are identified, as indicated at step 118. These outlier clusters are associated with observable, repeatable, but improbable (or rare) events. If desired, the probabilities associated with the outlier clusters can be used as prior inputs to a Bayesian Estimator to further refine the clusters, such as determining whether multiple clusters exist, as indicated at step 120. A report can then be generated based on the clusters, as indicated at step 122. As one example, the report can include data plots and other information depicting the clusters or analyses based on the clusters. For instance, the report can include data plots computed based on the clusters, such as a distribution of inter-spike intervals or other physiological parameters. The report can include an electronic display of such data or information, for example, by generating a display of the data or information on a suitable electronic display. In some embodiments, a report can be generated based on aggregated data across different channels (e.g., across different neurons) and/or comparing different channels.

Figure 3:
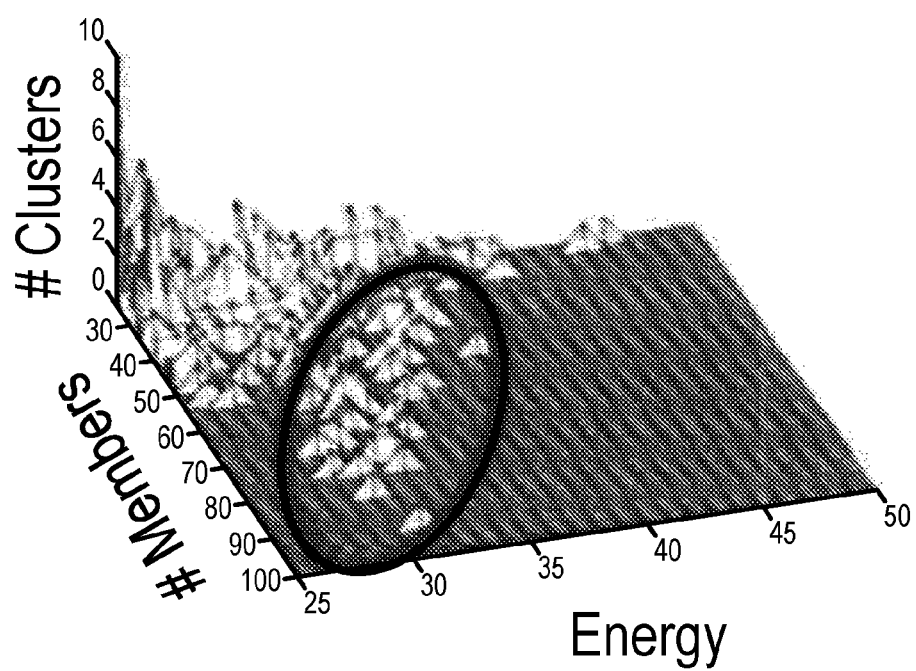
FIG. 3 is an example region-of-interest from the two-dimensional histogram of FIG. 2.
Figure 4:
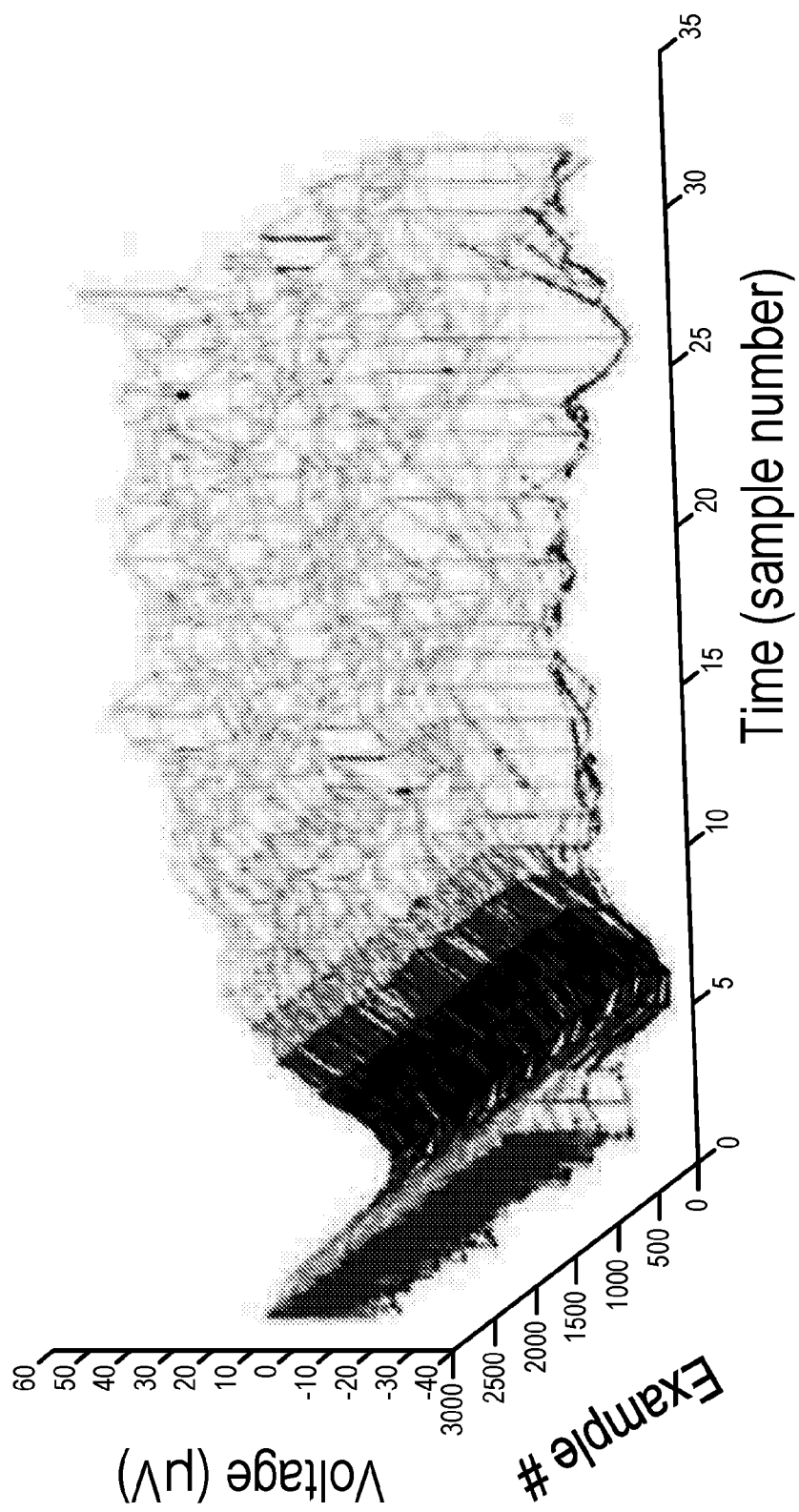
FIG. 4 is an example of waveforms associated with the region-of-interest of FIG. 3.
Figures 5, 6:
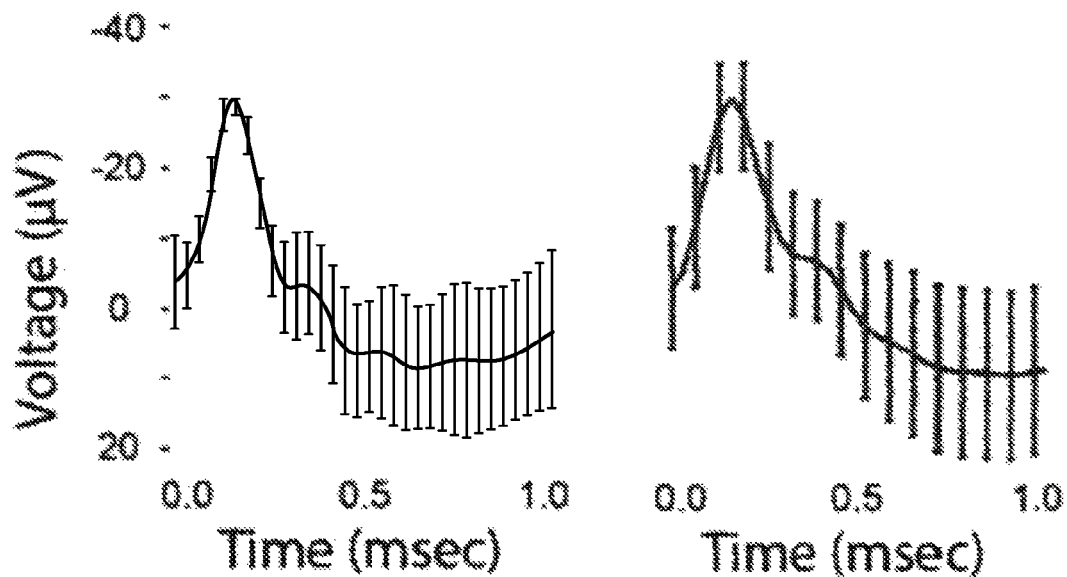
FIG. 5 is an example average waveform of the waveforms in FIG. 4.
FIG. 6 is another example average waveform of the waveforms in FIG. 4.
Figure 7:
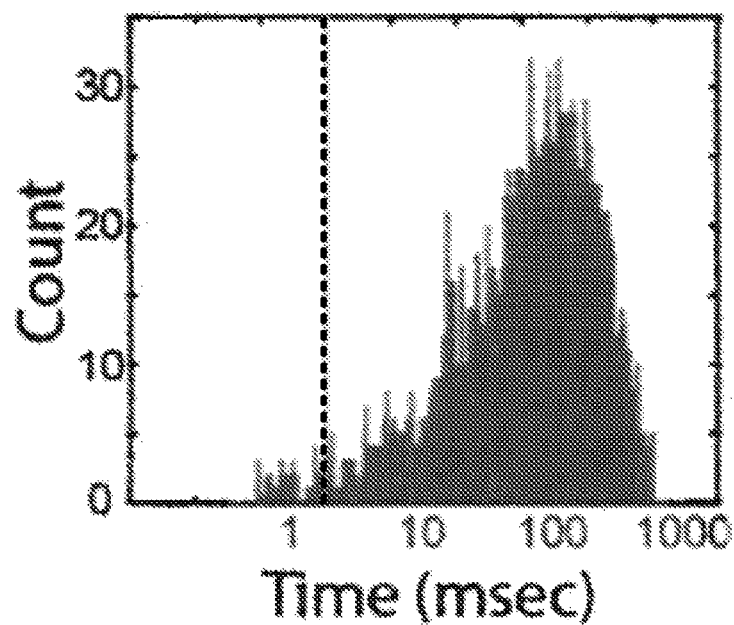
FIG. 7 is an example distribution of inter-spike interval data.

The outlier region identified in the example histogram of FIG. 2 is shown in detail in FIG. 3, and waveforms associated with the region noted by the ellipse in FIG. 3 are shown in FIG. 4. The average waveform of the outlier waveforms shown in FIG. 4 is shown in FIG. 5, where the error bars depict one standard deviation. As a comparison, the average waveform is depicted in FIG. 6 with error bars associated with one standard deviation for manual cutting of the same data. The inter-spike interval ("ISI") distribution of the waveforms in FIG. 4 is shown in FIG. 7. This distribution shows less than 0.1 percent of detections within a two millisecond "refractory period."

Using the techniques described herein can eliminate the need for at least three a priori assumptions required by currently available bounded time-signal clustering algorithms including those algorithms' assumption of fixed time-voltage detection thresholds, requirement for a guess at the number of initial clusters, and assumption that the waveform voltages are normally distributed.

These assumptions have been shown to be sub-optimal for extracellular waveform separation by K. D. Harris, et al., in "Accuracy of Tetrode Spike Separation as Determined by Simultaneous Intracellular and Extracellular Measurements," *Journal of Neurophysiology*, 2000; 84:401-414. However, no robust alternatives to these assumptions, or the algorithms built on them, have been proposed. The techniques described herein can utilize the entire continuous recording to accumulate statistics of all waveforms present on a given microwire, allowing a detailed model of the noise specific to that channel to be generated. Because the techniques described herein compute noise distributions based on observed data, the techniques described herein can facilitate adaptive approaches that can update the observed noise distribution and the probabilities of identified clusters.

Potential users of the techniques described herein can include the following groups of users: those who currently use identified, physiological signals, and those who would use such signals, if an automated, reliable solution existed. The former group includes clinicians, who use identifiable physiological signals for patient diagnosis. Examples include neurologists who identify sleep spindles in sleep studies or inter-ictal spikes in epilepsy studies. The latter group would include the neuroprosthetics field, where current technology emphasizes multi-unit, neuronal activity, because no automated, reliable methods exist to generate single-neuron activity.

Figure 8:
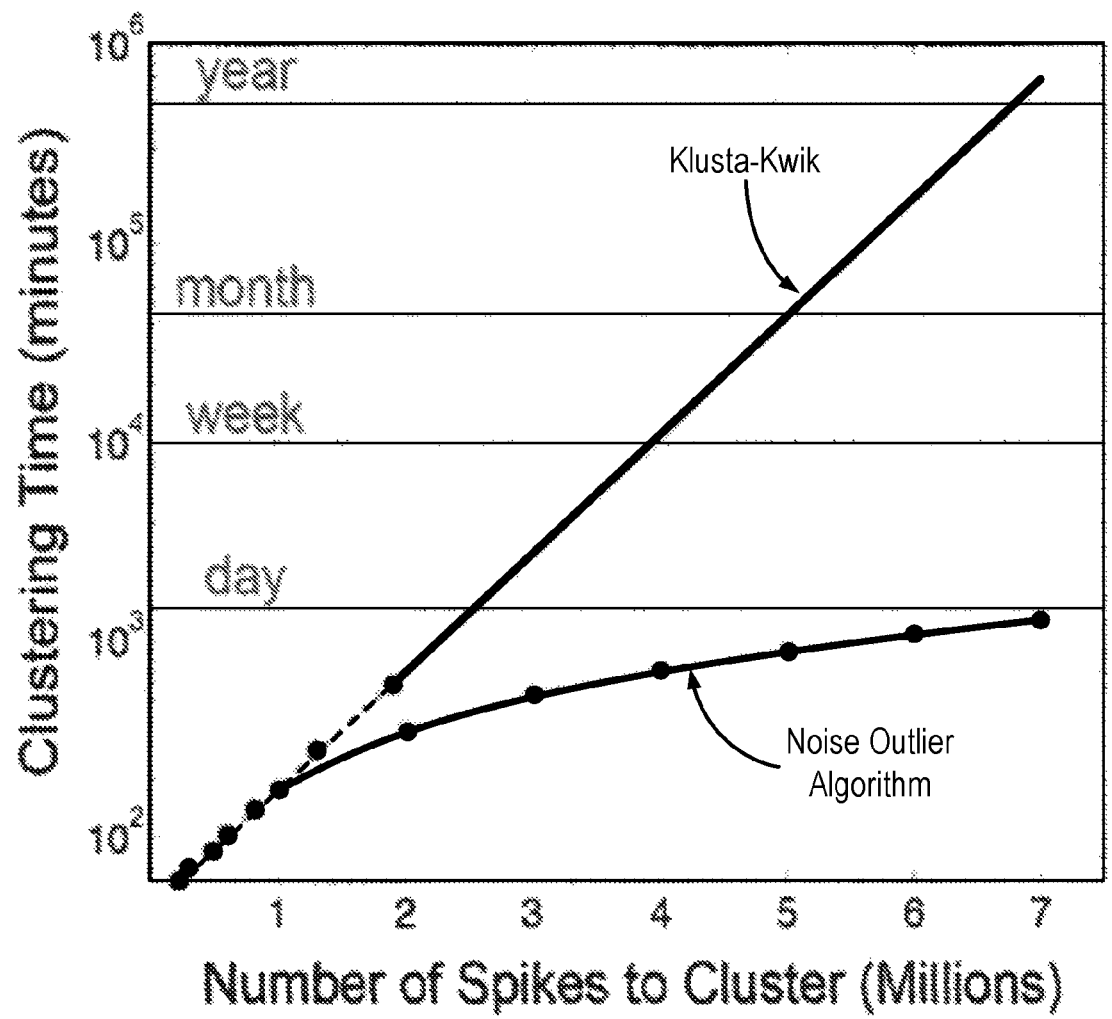
FIG. 8 is a data plot illustrating a comparison of a clustering process described herein and the Klusta-Kwik algorithm.

In an example study, the techniques described herein were compared to the "Klusta-Kwik" algorithm (Klusta-Team; University College London, UK), which is a popular optimization-based clustering algorithm that utilizes wave shape parameters. FIG. 8 illustrates (log scale) computational times for this comparison and depicts the actual time (dots and lines) and projection (dotted line) showing the increase in clustering time with increasing spike count. As shown, computational time for the Klusta-Kwik algorithm increased exponentially with spike number. Clustering time for the techniques described herein utilize waveform probabilities, instead of waveform features, and as a result are capable of computational time that scales linearly with increasing data points.

Figure 9:
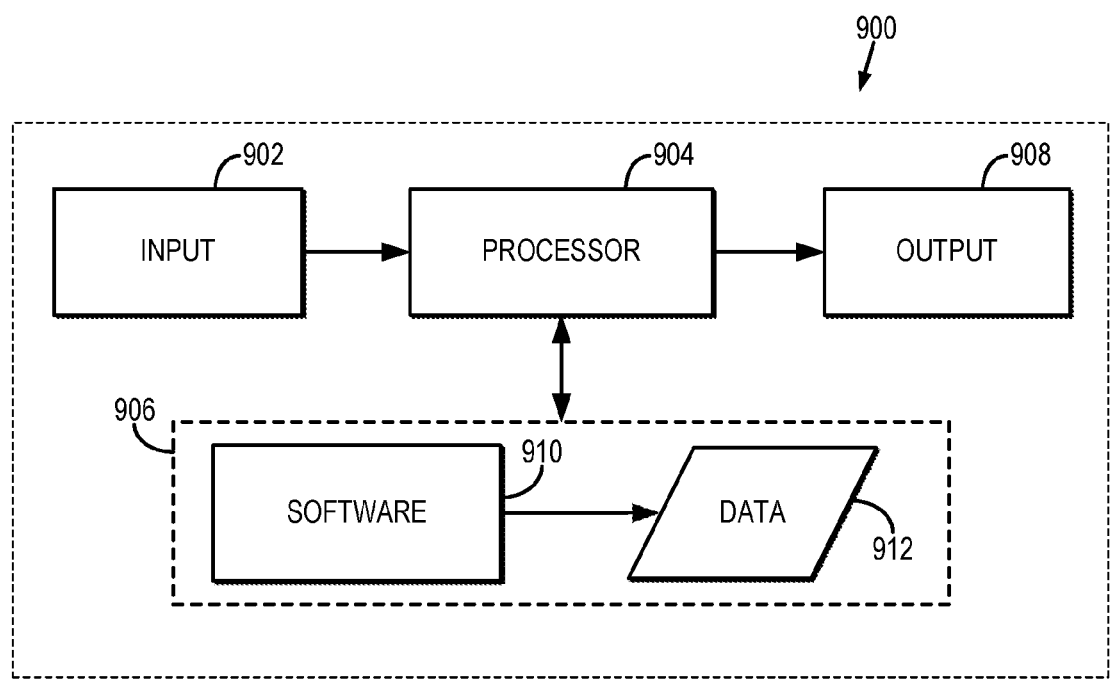
FIG. 9 is a block diagram of an example computer system that can be used to implement the processes described herein.

Referring now to FIG. 9, a block diagram is shown of an example computer system 900 for clustering events in physiological signal data, such as is described above in detail. The computer system 900 generally includes an input 902, at least one processor 904, a memory 906, and an output 908. The computer system 900 can also include any suitable device for reading computer-readable storage media. The computer system 900 may be, for example, a workstation, a notebook computer, a tablet device, a mobile device, a multimedia device, a network server, a mainframe, or any other general-purpose or application-specific computing device. The computer system 900 may operate autonomously or semi-autonomously, or may read executable software instructions from the memory 906 or a computer-readable medium (e.g., a hard drive, a CD-ROM, flash memory), or may receive instructions via the input 902 from a user, or any another source logically connected to a computer or device, such as another networked computer or server. In general, the computer system 900 is programmed or otherwise configured to implement the processes described above.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as physiological signals, or associated data. Such data may be processed as described above. In addition, the input 902 may also be configured to receive any other data or information considered useful for clustering events in physiological signal data.

Among the processing tasks for operating the computer system 900, the at least one processor 904 may also be configured to receive data, such as physiological signals, or associated data. In some configurations, the at least one processor 904 may also be configured to carry out any number of post-processing steps on data received by way of the input 902. In addition, the at least one processor 904 may be capable of clustering events in physiological signal data as described above.

The memory 906 may contain software 910 and data 912, and may be configured for storage and retrieval of processed information, instructions, and data to be processed by the at least one processor 904. In some aspects, the software 910 may contain instructions directed to clustering events in physiological signal data. Also, the data 912 may include any data necessary for operating the computer system 900, and may include any suitable physiological signal data as described above.

In addition, the output 908 may take any shape or form, as desired, and may be configured for displaying, in addition to other desired information, clustered physiological signal data or reports generated based on clustering of physiological signal data.

In some embodiments, any suitable number of computing systems can be used to perform different portions of the processes described herein. For example, a first computing system can be used to capture physiologic signal data, and provide that physiologic signal data to a second computing system (e.g., a server). In such an example, the second computing system can be used to analyze the physiologic signal data using the techniques described herein to determine which waveforms represent action potentials and which are likely to be noise. The second computing system can be used to generate one or more reports, graphics, etc., based on the analysis to and/or can send the results of the analysis to a third computing system (e.g., a personal computer, a tablet computer, a smartphone, another server, etc.). In such an example, the third computing device can be used to display the results of the analysis, generate one or more reports, graphics, etc., based on the analysis, display one or more reports, graphics, etc. received from the second computer, etc.

The present invention has been described in terms of one or more embodiments, and it should be appreciated that many equivalents, alternatives, variations, and modifications, aside from those expressly stated, are possible and within the scope of the invention.

The invention claimed is:

1. A method for identifying events of interest from noisy physiological signal data, the method comprising:
   (a) measuring extracellular electrical activity of a neuron using a microwire;
   (b) receiving, by a computing system, physiological signal data from the microwire, wherein the physiological signal data represents the measured extracellular electrical activity;
   (c) filtering the physiological signal data using a filter defined by a spectral band associated with a particular physiological event to generate filtered signal data;
   (d) identifying with the computer system, for each of a plurality of time windows in the filtered signal data, a signal peak in the filtered data to generate signal peak data;
   (e) grouping waveforms from the physiological signal data corresponding to each of the plurality of time windows based on the signal peak data to generate clustered event data;
   (f) determining parameters for a noise beta distribution based at least in part on the signal peak data;
   (g) identifying at least one cluster of waveforms from the clustered event data that does not fall within the noise beta distribution, wherein each waveform in the at least one cluster represents a physiological events of interest in the physiological signal data;
   (h) generating a graphical representation based on the waveforms in the at least one cluster of waveforms; and
   (i) causing the graphical representation to be displayed.

2. The method of claim 1, wherein the physiologic signal data represents extracellular electrical activity of a single neuron.

3. The method of claim 2, wherein the physiologic signal data is received from at most a single microwire.

4. The method of claim 2, wherein the graphical representation shows a plurality of the waveforms in the at least one cluster of waveforms.

5. The method of claim 2, wherein the graphical representation shows an average waveform that represents a plurality of the waveforms in the at least one cluster of waveforms.

6. The method of claim 2, wherein the physiologic signal data represents at least twenty four hours of signals.

7. The method of claim 2, wherein the spectral band is from about 600 Hertz to about 6,000 Hertz.

8. The method of claim 2, wherein the time window is about one millisecond.

9. The method of claim 2, the method further comprising repeating (a) through (h) for second physiologic signal data that represents an extracellular recording of electrical activity of a second single neuron.

10. The method of claim 1, wherein generating signal peak data further comprises generating an N×1 vector, where N is the number of time windows in the plurality of time windows.

11. The method of claim 10, wherein each value in the N×1 vector represents the peak value of the physiologic signal in a particular time window.

12. The method of claim 11, wherein grouping the waveforms from the physiological signal data further comprises grouping waveforms corresponding to time windows having similar values in the N×1 vector.

13. The method of claim 1, further comprising:
   using probabilities associated with the at least one cluster as an input to a Bayesian Estimator; and
   identifying, based on the output of the Bayesian estimator, a second cluster of waveforms from the clustered event data that does fall within the noise beta distribution as likely representing physiological events of interest in the physiological signal data.

14. A system for identifying events of interest from noisy physiological signal data, the system comprising:
   a display;
   a microwire configured to measure electrical activity of a neuron; and
   a hardware processor that is programmed to:
      (a) receive physiological signal data from the microwire;

(b) filter the physiological signal data using a filter defined by a spectral band associated with a particular physiological event to generate filtered signal data;

(c) identify with the computer system, for each of a plurality of time windows in the filtered signal data, a signal peak in the filtered data to generate signal peak data;

(d) group waveforms from the physiological signal data corresponding to each of the plurality of time windows based on the signal peak data to generate clustered event data;

(e) determine parameters for a noise beta distribution based at least in part on the signal peak data;

(f) identify at least one cluster of waveforms from the clustered event data that does not fall within the noise beta distribution, wherein each waveform in the at least one cluster represents a physiological events of interest in the physiological signal data;

(g) generate a graphical representation based on the waveforms in the at least one cluster of waveforms; and (h) cause the graphical representation to be displayed using the display.

15. The system of claim 14, wherein the physiologic signal data represents an extracellular recording of electrical activity of a single neuron.

16. The system of claim 15, wherein the graphical representation shows a plurality of the waveforms in the at least one cluster of waveforms.

17. The system of claim 15, wherein the graphical representation shows an average waveform that represents a plurality of the waveforms in the at least one cluster of waveforms.

18. The system of claim 15, wherein the physiologic signal data represents at least twenty four hours of signals.

19. The system of claim 15, wherein the spectral band is from about 600 Hertz to about 6,000 Hertz.

20. The system of claim 15, wherein the time window is about one millisecond.

* * * * *